(12) United States Patent
Sembritzki et al.

(10) Patent No.: US 6,650,726 B2
(45) Date of Patent: Nov. 18, 2003

(54) METHOD FOR PRODUCING AN IMAGE BY COMPUTER TOMOGRAPHY

(75) Inventors: Otto Sembritzki, Wachenroth (DE); Heinrigh Wallschlaeger, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/147,005

(22) Filed: May 15, 2002

(65) Prior Publication Data

US 2002/0172321 A1 Nov. 21, 2002

(30) Foreign Application Priority Data

May 16, 2001 (DE) .......................................... 101 23 797

(51) Int. Cl.⁷ .............................................. G01N 23/00
(52) U.S. Cl. ................................................. 378/8; 378/4
(58) Field of Search .......................................... 378/8, 4

(56) References Cited

U.S. PATENT DOCUMENTS 5,991,356 A * 11/1999 Horiuchi et al. ............... 378/8
6,381,487 B1   4/2002 Flohr et al.

OTHER PUBLICATIONS

"Bildebende Systeme Für die Medizinische Diagnostik," Heinz Morneburg (1995), pp. 136–137.

* cited by examiner

Primary Examiner—Craig E. Church
(74) Attorney, Agent, or Firm—Schiff Hardin & Waite

(57) ABSTRACT

In a method for producing an image of an examination subject by computed tomography using an x-ray source that moves around the examination subject for producing the image, a number of projections serving for the production of the image are registered during at least one revolution of the x-ray source around the examination subject. Motion artifacts of the image are at least reduced by identifying data representing a part of the image exhibiting a motion, and replacing that data with data complementary to the data exhibiting movement.

4 Claims, 4 Drawing Sheets

METHOD FOR PRODUCING AN IMAGE BY COMPUTER TOMOGRAPHY

BACKGROUND OF THE INVENTION

1. Field of the Invention

The present invention is directed to a method for producing an image of an examination subject by computed tomography wherein an X-ray source that moves around the examination subject for the production of the image.

2. Description of the Prior Art

In a computed tomography, projections are registered from the examination subject while an x-ray source moves around the examination subject, Data allocated to these projections are employed for the production of the image If the examination subject or parts of the examination subject move while the projections are being registered, the image can exhibit motion artifacts that can result in an unsharp image. This problem occurs particularly in images of the heart or of heart-proximate lung structures when the projections were registered during the rapid contraction phase of the heart.

In order to at least alleviate motion artifacts when registering the heart or heart-proximate lung structures, German OS 198 54 939 discloses a method for generating CT images of a body region having quiescent and motion phases and moving periodically by means of a CT apparatus having an x-ray source moved around the body of the life form to be examined. In this method, projections for image reconstruction employ only data allocated to the projections that were acquired during a quiescent phase.

A disadvantage of this method, however, is that it is limited to a motion of a body region that moves periodically with quiescent or motion phases.

Morneburg (editor), "Bildgebende Systeme für die medizinische Diagnostik", Publicis MCD Verlag, Erlangen, 1995, pages 136 and 137, describes a method for reducing motion artifacts that is also suitable for non-periodic movements of the examination subject or parts of the examination subject The movements, for example, are generated by peristaltics, respiration, tremor or general unrest on the part of the examination subject or parts of the examination subject.

In this method, referred to as the multi-scan technique, the x-ray source moves repeatedly around the examination subject and the data allocated to the projections are subsequently averaged Motion artifacts that occur are reduced as a result. A disadvantage of this method is the increased radiation dose that the examination subject is exposed to due to the multiple movement of the x-ray source around the examination subject. Further, data that are allocated to a movement of the examination subject are also employed for the production of the image.

SUMMARY OF THE INVENTION

An object of the invention is to provide a method that creates pre-requisites for alleviating negative influences of a not necessarily periodic movement of the examination subject or parts of the examination subject during the registration of the projections The object is achieved in a method for producing an image of an examination subject by computed tomography wherein an x-ray source moves around the examination subject for producing the image, wherein a number of projections serving for the production of the image are registered during at least one revolution of the x-ray source around the examination subject, comprising the following method steps:

a) determining those data of the projections that are falsified by a movement of the examination subject; and b) replacing at least the data of a projection falsified by the movement of the examination subject by the data complementary thereto.

In the inventive method, thus, projections are registered from the examination subject during at least one revolution of the x-ray source around the examination subject. Subsequently, the data allocated to the projections that are falsified by the movement of the examination subject are identified and are replaced by their complementary data. The data and their complementary data can, for example, be acquired from projections in parallel geometry, with the projections that are allocated to the data or their complementary data exhibiting a projection angle offset by 180°. Since modern computed tomography systems usually register fan projections, parallel projections are generated therefrom only by suitable interpolation rules and resorting rules, for example by the known technique of re-binning. A parallel projection is then composed of measured values of fan projections measured at different points in time. For example, the measuring point in time of a central channel can then be defined as measuring point in time of a parallel projection.

An advantage of inventive method is that only data that are not falsified by a movement of the examination subject or parts of the examination subject are employed for producing the image. It is thus not necessary that the movement of the examination subject ensue periodically.

In order to identify the falsified data, a deviation of the data of a projection from its complementary data is determined according to one version of the invention, wherein data or their complementary data are considered falsified when the deviation exceeds an upper limit value $\sigma_s$. The background of this consideration is that data of a projection and their complementary data are identical given an immobile examination subject. A deviation of the data of a projection from their complementary data, thus, is an indicator for the movement of the examination subject.

In a preferred version of the invention, parallel coordinates are allocated to the projections. The deviation of the data of the projection from their complementary data is determined according to the following method:

a) calculating difference signals $\Delta S_1(\theta, p)$ from the data of the projection and their complementary data for each projection angle $\theta$ between 0 and $\pi$ of the projection and each channel p$\epsilon$[v, P] according to the following equation:

$$\Delta S_1(\theta, p) = S(\theta, p) - S(\theta + \pi, -p) \quad (1)$$

whereby the signals $S(\theta, p)$ are allocated to the projections for projection angles $\theta$ between 0 and $\pi$ and the signals $S(\theta + \pi, -p)$ are allocated to their complementary data; and b) calculating the deviation as standard deviation $\sigma_1(\theta)$ of the difference signals $\Delta S_1(\theta, p)$ for each projection angle $\theta$ between 0 and $\pi$ via the channels p$\epsilon$[$P_S$, $P_{74}$] according to the following equation:

$$\sigma_1(\theta) = \sigma_p\{\Delta S_1(\theta, p)\}, \quad (2)$$

whereby $[P_s, P_e] \subset [-P, P]$.

Inventively, thus, difference signals $\Delta S_1(\theta, p)$ are formed for each projection angle $\theta$ between 0 and $\pi$ and for each channel p$\epsilon$[-P, P]. Subsequently, the standard deviation $\sigma_1(\theta)$ of the difference signals $\Delta S_1(\theta, p)$ is formed. The standard deviation $\sigma_1(\theta)$ can be inventively formed over all channels p$\epsilon$[-P, P]. When data of a projection are falsified due to a movement on the part of the examination subject, thus, all data of this projection are replaced by their complementary data. The standard deviation a(e), however, also can be formed over sub-regions [$P_s$, $P_\theta$] of the channels p. Then, in particular, locally limited motion artifacts, i.e. movements on the part of sub-regions of the examination subject, can be discovered and the data falsified as a result can be limited in the projection. As a result, it is possible to replace only the data of the projection falsified due to the partial movement of the examination subject by their complementary data.

Whether the data of the projection or their complementary data are falsified by the movement of the examination subject, however, cannot be recognized on the basis of the determination of the deviation of the data of a projection from their complementary data. Another allocation is thus necessary as to whether the falsified data are allocated to a projection angle $\theta$ between 0 and $\pi$ or to a projection angle $\theta$ between $\pi$ and $2\pi$. According to one embodiment of the invention, the deviations of the data of a projection from data of the following projection are therefore determined for all projection angles $\theta$ that are allocated to at least one revolution of the x-ray source. Further, a projection angle $\theta_{max}$ is determined that corresponds to the maximum deviation of the deviations. The falsified data then have projection angles $\theta$ between 0 and $\pi$ allocated to them when $\theta_{max}$ lies between 0 and $\pi$ and the falsified data are allocated to projection angles $\theta$ between $\pi$ and $2\pi$ when $\theta_{max}$ lies between $\pi$ and $2\pi$.

According to a preferred version of the invention, parallel coordinates are allocated to the projections. The deviations of the data of a projection from data of the following projection are determined according to the following method:

a) calculating difference signals $\Delta S_2(\theta, p)$ from data of a projection and data of its following projection for each projection angle $\theta$ between $\Delta\theta$ and $2\pi$ and each channel p∈[−P, P], whereby the projection angles $\theta$ of the projection and its following projection differ by $\Delta\theta$, according to the following equation:

$$\Delta S_2(\theta,p)=S(\theta, p)-S(\theta-\Delta\theta, p) \text{ and} \quad (3)$$

b) calculating the deviation as standard deviation $\sigma_2(\theta)$ of the difference signals $\Delta S_2(\theta, p)$ for each projection angle $\theta$ between $\Delta\theta$ and $2\pi$ over the channels p∈[−P, P] according to the following equation:

$$\sigma_2(\theta)=\sigma_p\{\Delta S_2(\theta,p)\} \quad (4)$$

DESCRIPTION OF THE PREFERRED EMBODIMENTS

Figure 1:
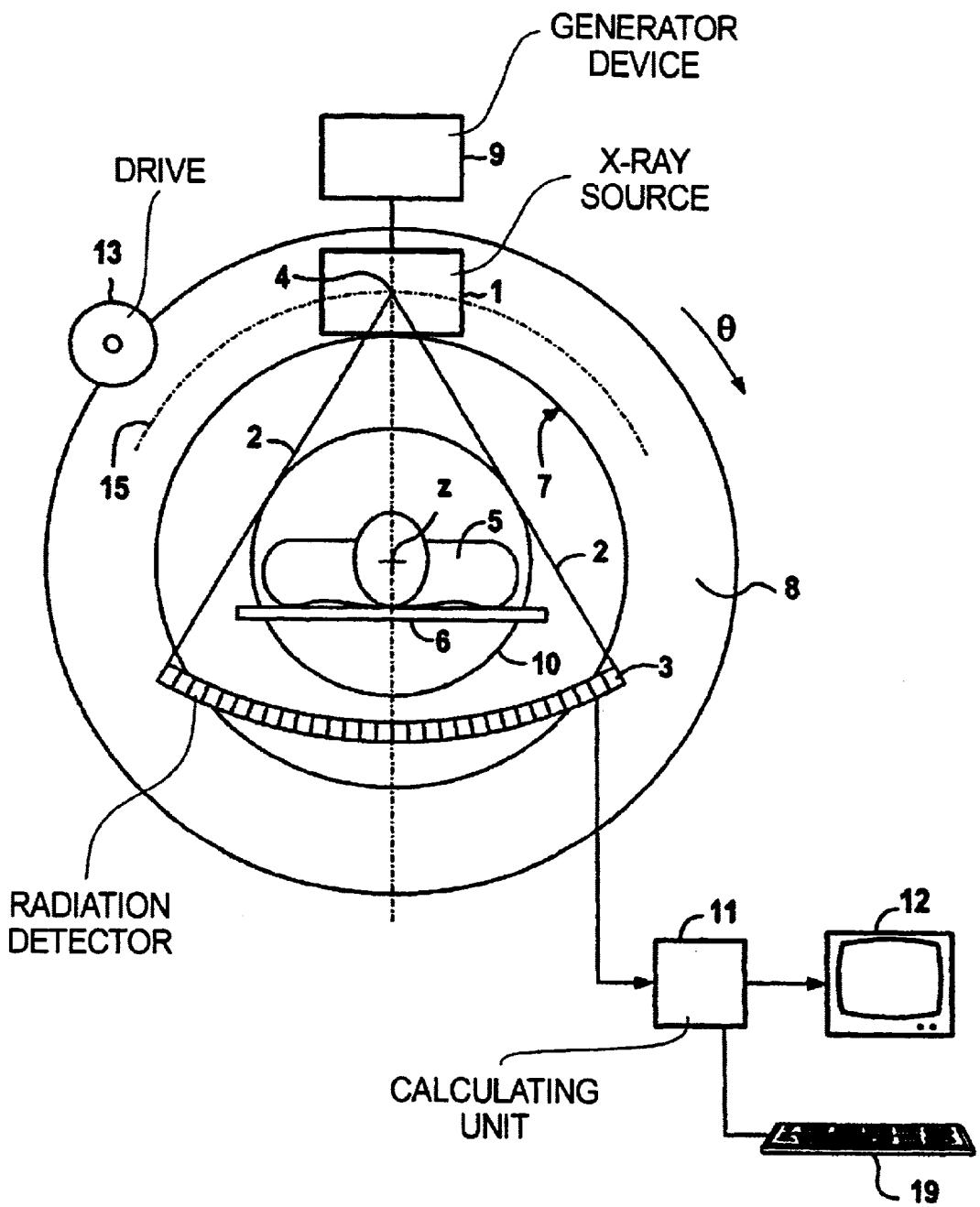
FIG. 1 illustrates a computed tomography apparatus suitable for the implementation of the inventive method

The computed tomography apparatus schematically illustrated in FIG. 1 has a measurement unit composed of an x-ray source 1 that emits a fan-shaped x-ray beam 2, and a detector 3 that is composed of a detector line with 512 individual detectors. The focus of the x-ray source 1 from which the x-ray beam 1 emanates is referenced 4. An examination subject, a human patient 5 in the case of the illustrated exemplary embodiment, lies on a support table 6 that extends through the measurement opening 7 of a gantry 8.

The x-ray source 1 and the detector 3 are attached to the gantry 8 opposite one another. The gantry 8 is rotatably seated around the z-axis of the computed tomography apparatus (referenced z) that represents the system axis, and is rotated around the 7-axis in the direction of the arrow o for scanning the patient 5 in the $\theta$ direction, namely by an angle that amounts to at least equal to 360° ($2\pi$). The x-ray beam 2 emanating from the x-ray source 1 operated by a generator device 9 covers a measurement field 10 having a circular cross-section. The focus 4 of the x-ray source 1 moves on a circularly curved focus path 15 around a rotational center lying on the z-axis.

Measured values in the form of projections are registered at certain angular positions of the measurement unit 1, 3, referred to as the projection angles $\theta$, and the corresponding data proceed from the detector 3 to a calculating device 11 In the case of the present exemplary embodiment, the measurement system 1, 3 is configured for a projection angle $\theta=0$, as shown in FIG. 1, i.e. the x-ray source 1 and the detector 3 are aligned vertically relative to one another, with the x-ray source 1 being aligned above the detector 3. Further, the measurement unit 1, 3 moves around the patient 5 in the direction of the arrow $\theta$, so that a total of 1500 projections are registered in the case of the exemplary embodiment during an entire revolution of the measurement unit 1, 3 around the patient 5 with various projection angles $\theta$. The projection angles $\theta$ of two successive projections thereby differ by an angular range $\Delta\theta$.

When the drive 13 allocated to the gantry 8 is inadequate for a full revolution of the gantry 8 but is suited for allowing the gantry 8 to rotate continuously and, moreover, a further drive (not shown in FIG. 1) is provided that enables a relative displacement between the support table 6, and thus the patient 5, and of the gantry 8 with the measurement unit 1, 3 in the z-direction, spiral scans can be implemented.

In the exemplary embodiment, the calculating device 11 calculates parallel projections from the data allocated to the projections by means of the known re-binning method. Using these parallel projections, the calculating device 11—in a first operating mode-produces images of the slices of the patient 5 covered by the projection in a known way, these images being reproduced on a monitor 12. Such an image is shown as an example in FIG. 2. The image shows an exposure of the cervical spine of the patient 5 in the standard sequence technique with 1500 parallel projections over a projection angular range of 360° ($2\pi$). In the exemplary embodiment, the image shown in FIG. 2 contains motion artifacts due to a partial movement on the part of the patient 5, these being bounded by a rectangle 20 mixed into the image shown in FIG. 2, In a second operating mode, which can be activated with a keyboard 19 that is connected to the calculating device 11, the calculating device 11 produces an image on the basis of the inventive method.

In the exemplary embodiment, the calculating device 11 uses a suitable computer program to calculate difference signals $\Delta S_1(\theta, p)$ from the parallel projections generated by means of the re-binning method for each projection angle $\theta$ between 0 and $\pi$ and for each channel p of the detector 3 according to $$\Delta S_1(\theta, p)=S(\theta,p)-S(\theta+\pi,-p) \quad (1)$$

whereby the signals $S(\theta, p)$ are allocated to the projections for projection angles $\theta$ between 0 and $\pi$, and the signals $S(\theta+\pi_1-p)$ are allocated to the data complementary thereto.

Subsequently, the calculating device 11 uses the computer program to calculate the standard deviation $\sigma_1(\theta)$ of the difference signals $\Delta S_1(\theta, p)$ for each projection angle $\theta$ over all channels p of the detector according to $$\sigma_1(\theta)=_p\{\Delta S_1(\theta,p)\} \quad (2)$$

After this, the calculating device 11 uses the computer program to compare the standard deviation $\sigma_1(\theta)$ for each projection angle $\theta$ to an upper limit value $\sigma_5$. If the standard deviation $\sigma_1(\theta)$ exceeds the upper limit value $\sigma_s$, then data or their complementary data of the appertaining projections with the corresponding projection angle $\theta$ are considered falsified As a result, the calculating device 11 recognizes a projection angle range $\theta_1$ through $\theta_2$ with the computer program in that the data allocated to these projections are falsified on the basis of a movement on the part of the patient 5.

Equations 1 and 2, however, do not yet provide any information about whether the data falsified due to the movement on the part of the patient 5 are allocated to a projection angle range from 0 through $\pi$ or to a projection angle range from $\pi$ through $2\pi$, the equations 1 and 2 do not yet provide information as to whether $[\theta_1, \theta_2] \subset [0, \pi]$ or $[\theta_1, \theta_2]_{\subset [\pi,} 2\pi]$ applies. The calculating device 11 therefore uses the computer program to calculate further difference signals $\Delta S_2$ ($\theta$, p) from the data of a projection and the data of its following projection for each projection angle $\theta$ between as and $2\pi$ and each channel p, whereby the projection angles $\theta$ of the projection and its following projection differ by $\Delta\theta$. The difference signals $\Delta S_2$ ($\theta$, p) are calculated according to $$\Delta S_2(\theta, p) = S(\theta, p) - S(\theta - \Delta\theta, p) \quad (3)$$

Subsequently, the calculating unit 11 uses the computer program to calculate a further standard deviation $\sigma_2(\theta)$ of the difference signals $\Delta S_2$ ($\theta$, p) for each projection angle $\theta$ between $\Delta\theta$ and $2\pi$ over all channels p according to $$\sigma_2(\theta) = \sigma_p \{\Delta S_2(\theta, p)\} \quad (4)$$

Using the calculated standard deviations $\sigma_2(\theta)$ for each projection angle $\theta$ between $\Delta\theta$ and $2\pi$, the calculating device 11 determines that projection angle $\theta_{max}$ for which the standard deviation $\sigma_2(\theta)$ is maximum. When $\theta_{max}$ now lies between 0 and $\pi$, data for projection angles $\theta$ between 0 and $\pi$ are falsified. When $\theta_{max}$ lies between $\pi$ and $2\pi$, data for projection angles $\theta$ between $\pi$ and $2\pi$ are falsified. Consequently, data in a projection angle range $[\theta_1, \theta_2] \subset [0, \pi]$ are falsified when $\theta_{max} \in [0, \pi]$ applies, or are falsified in a projection angle range $[\theta_1, \theta_2] \subset [\pi, 2\pi]$ when $\theta_{max} \in [\pi, 2\pi]$ applies.

Subsequently, the data of the falsified projections are replaced by their complementary data When $\theta_{max} \in [0, \pi]$ applies, then the signals $S(\theta, p)$ are replaced by the signals $S(\theta + \pi, -p)$, and when $\theta_{max} \in [\pi, 2\pi]$ applies, then the signals $S(\theta + \pi, -p)$ are replaced by the signals $S(\theta, p)$, whereby $\theta \in ([\theta_1, \theta_2] \mod \pi)$ applies.

Figure 2:
FIG. 2 is an image having motion artifacts.
Figure 3:
FIG. 3 is an image produced with the inventive method.

FIG. 3 shows an example of an image produced on the basis of the inventive method The image shown in FIG. 3 corresponds to the image shown in FIG. 2, wherein the data falsified due to the movement on the part of the patient 5 have been replaced by their complimentary data according to Equation 5. The image shown in FIG. 3 was additionally corrected in the linear transition region between the falsified and the unfalsified data of 40 projections and overall channels, by forming weighted averages from the data of the projections and their complimentary data.

Figure 4:
FIG. 4 is an image wherein a movement is intensified.

A further operating mode is also provided in the exemplary embodiment, in which the calculating device 11 uses a suitable computer program to calculate a difference image from images acquired by the computed tomography apparatus, with the inventive method not being applied for the one image and being applied for the other. This difference image corresponds to the motion part of the movement on the part of the patient 5. Subsequently, the computing device 11 uses the computer program to add this difference image to the image that was not produced by means of the inventive method. The image that has arisen in this way thus images the motion part intensified. FIG. 4 shows an image that was produced by means of the images shown in FIGS. 2 and 3.

A sequence of three images can be generated with this method. The first image is without motion part (see the image shown in FIG. 3), the second image is with motion part (see the image shown in FIG. 2), and the third image is restricted to the motion part (see the image shown in FIG. 4). The motion of the patient 5 can be presented in a rapid sequence of these three images.

In order, in particular, to acquire locally limited movements on the part of the patient 5 and to limit the data of the allocated projection falsified as a result thereof, the standard deviation $\sigma_1(\theta)$ in a further operating mode is determined only over a sub-region $[P_s, P_E]$ of the channels p of the detector 3, Only the sub-region of the channels of the corresponding projection affected by the movement on the part of the patient 5 are thus determined. This channel region can fluctuate from projection to projection. As a result, the correction can be limited to a very small area and optimum quantum utilization can be achieved given locally limited motion artifacts such as, for example, aorta pulsation.

The inventive method was described on the basis of a computed tomography apparatus having a single-slice detector 3, but it can also be employed for a computed tomography apparatus having a multi-slice detector. In this case, a number of slices of the patient 5 can be simultaneously registered as needed, whereby a number of projections corresponding to the number of activated detector slices being registered per projection angle $\theta$.

The examination subject need not necessarily be a human patient 5. The method can also be applied to animals or to articles as well.

Although modifications and changes may be suggested by those skilled in the art, it is in the intention of the inventors to embody within the patent warranted hereon all changes and modifications as reasonably and properly come within the scope of their contribution to the art.

We claim as our invention:

1. A method for producing an image of an examination subject by computed tomography by rotating an x-ray source around an examination subject with a plurality of projections for production of the image being registered during at least one revolution of the x-ray source around the examination subject, comprising the steps of:

determining data in said projections that are falsified by a movement of the examination subject solely by identifying a deviation of the data of a projection from their complementary data and designating said data or their complementary data as falsified if the deviation exceeds an upper limit value; and replacing at least the data of a projection falsified by the movement of the examination subject with the data complementary thereto.

2. A method as claimed in claim 1, comprising allocating parallel coordinates to the projections and identifying said deviation of the data of the projection from their complementary data by the steps of:

calculating difference signals $\Delta S_1(\theta, p)$ from the data of the projection and their complementary data for each projection angle $\theta$ between 0 and $\pi$ of the projection and each channel $p \in [-P, P]$ according to the equation:

$$\Delta S_1(\theta, p) = S(\theta, p) - S(\theta + \pi, -p),$$

wherein the signals $S(\theta, p)$ are allocated to the projections for projection angles $\theta$ between 0 and $\pi$ and the signals $S(\theta+\pi, -p)$ are allocated to their complementary data; and calculating said deviation as a standard deviation $\sigma_1(\theta)$ of the difference signals $\Delta S_1(\theta, p)$ for each projection angle $\theta$ between 0 and $\pi$ via the channels $p \in [P_s, P_e]$ according to the equation:

$$\sigma_1(\theta) = \sigma_p\{\Delta S_1(\theta, p)\},$$

wherein $[P_s, P_e] \subset [-P, P]$.

3. A method as claimed in claim 1 comprising identifying said deviation by identifying deviations of the data of a projection from data of a following projection for all projection angles ($\theta$) that are allocated to at least one revolution of the x-ray source, determining a projection angle $\theta_{max}$ that corresponds to a maximum deviation of said deviations, and allocating projection angles ($\theta$) between 0 and $\pi$ to the falsified data when $\theta_{max}$ lies between 0 and $\pi$ and allocating projection angles ($\theta$) between $\pi$ and $2\pi$ to the falsified data when $\theta_{max}$ lies between $\pi$ and $2\pi$.

4. A method as claimed in claim 3, comprising allocating parallel coordinates to the projections and determining said deviations of the data of a projection from data of the following projection by the steps of:

calculating difference signals $\Delta S_2(\theta, p)$ from data of a projection and data of the following projection for each projection angle $\theta$ between $\Delta\theta$ and $2\pi$ and each channel $p \in [-P, P]$, the projection angles $\theta$ of the projection and the following projection differing by $\Delta\theta$, according to the equation:

$$\Delta S_2(\theta, p) = S(\theta, p) - S(\theta - \Delta\theta, p); \text{ and}$$

calculating said deviation as a standard deviation $\sigma_2(\theta)$ of the difference signals $\Delta S_2(\theta, p)$ for each projection angle $\theta$ between $\Delta\theta$ and $2\pi$ over the channels $p \in [-P, P]$ according to the equation:

$$\sigma_2(\theta) = \sigma_p\{\Delta S_2(\theta, p)\}.$$

* * * * *